United States Patent
Kim et al.

(10) Patent No.: US 11,478,523 B2
(45) Date of Patent: Oct. 25, 2022

(54) ORIENTAL MEDICINE COMPOSITION EFFECTIVE FOR THYROID HORMONE LEVEL NORMALIZATION

(71) Applicant: Hyong Jun Kim, Seoul (KR)

(72) Inventors: Hyong Jun Kim, Seoul (KR); Sung Sook Kim, Seoul (KR)

( * ) Notice: Subject to any disclaimer, the term of this patent is extended or adjusted under 35 U.S.C. 154(b) by 85 days.

(21) Appl. No.: 16/811,849

(22) Filed: Mar. 6, 2020

(65) Prior Publication Data

US 2020/0306332 A1   Oct. 1, 2020

(30) Foreign Application Priority Data

Mar. 27, 2019   (KR) .................. 10-2019-0035011

(51) Int. Cl.
| | |
|---|---|
| *A61K 36/804* | (2006.01) |
| *A61K 36/232* | (2006.01) |
| *A61K 36/815* | (2006.01) |
| *A61K 36/65* | (2006.01) |
| *A61K 36/8945* | (2006.01) |
| *A61K 36/284* | (2006.01) |
| *A61K 36/8964* | (2006.01) |
| *A61K 36/756* | (2006.01) |
| *A61K 36/484* | (2006.01) |
| *A61K 36/076* | (2006.01) |
| *A23L 33/105* | (2016.01) |

(52) U.S. Cl.
CPC .......... *A61K 36/804* (2013.01); *A23L 33/105* (2016.08); *A61K 36/076* (2013.01); *A61K 36/232* (2013.01); *A61K 36/284* (2013.01); *A61K 36/484* (2013.01); *A61K 36/65* (2013.01); *A61K 36/756* (2013.01); *A61K 36/815* (2013.01); *A61K 36/8945* (2013.01); *A61K 36/8964* (2013.01)

(58) Field of Classification Search
None
See application file for complete search history.

(56) References Cited

U.S. PATENT DOCUMENTS 7,691,419 B2 * 4/2010 DiLeva .................. A61Q 17/00
424/766

FOREIGN PATENT DOCUMENTS

| CN | 103800728 A | * | 5/2014 |
|---|---|---|---|
| CN | 103800728 A | | 5/2014 |
| CN | 104324206 A | | 2/2015 |
| CN | 106421430 A | | 2/2017 |
| KR | 1020060030575 | | 4/2006 |
| KR | 10-1771521 B1 | | 8/2017 |
| KR | 101771521 B1 | * | 8/2017 |

OTHER PUBLICATIONS

KR 10-1771521, KIPRIS machine translation, kpat.kipris.or.kr/pmt/patent/patentRTT.jsp accessed Sep. 21, 2021.*
Office Action, dated Jun. 11, 2020, KR 10-2019-0035011.
Korean Notice of Allowance dated Dec. 21, 2020, issued by the KIPO in the Korean Priority Application No. 10-2019-0035011.

* cited by examiner

*Primary Examiner* — H. Sarah Park

(74) *Attorney, Agent, or Firm* — Henry J. Cittone; Cittone Demers & Arneri LLP

(57) ABSTRACT

The present disclosure relates to an oriental medicine composition effective for thyroid hormone level normalization, and more particularly, to an oriental medicine composition for treating thyroid diseases, such as hypothyroidism or hyperthyroidism.

4 Claims, 5 Drawing Sheets

ORIENTAL MEDICINE COMPOSITION EFFECTIVE FOR THYROID HORMONE LEVEL NORMALIZATION

CROSS-REFERENCE TO RELATED APPLICATION

This application claims priority to Korean Patent Application No. 10-2019-0035011 filed on Mar. 27, 2019 in the Korean Intellectual Property Office, the contents of which in its entirety are herein incorporated by reference.

BACKGROUND

Field

The present disclosure relates to an oriental medicine composition effective for thyroid hormone level normalization, and more particularly, to an oriental medicine composition for treating thyroid diseases, such as hypothyroidism or hyperthyroidism.

Description of the Related Art

Thyroid related disease, specifically hypothyroidism, is a common endocrine disorder that occurs in approximately 4 to 15% of the population worldwide. The prevalence of hypothyroidism in Korea is approximately 14% of the population. The hypothyroidism results from the malfunction of thyroid gland producing an essential amount of thyroid hormones, and primary symptoms of the hypothyroidism include dry skin, increased sensitivity to cold, chronic fatigue, muscle cramps, constipation and hoarseness.

As one of conventional methods for treatment of hypothyroidism, levothyroxine supplement treatment has been usually employed. In the case of administering levothyroxine to a patient, thyroid hormone level normalization can be maintained by replacing deficient thyroid hormone with levothyroxine.

However, if the exact dosage of levothyroxine is not kept, side effects, such as vomiting, diarrhea, or headache, may be caused. In addition, while the level of thyroid stimulating hormone (TSH) is mostly normalized, some of the symptoms of hypothyroidism, such as neurologic disorders, may not be entirely eliminated. Accordingly, there have been continuous demands for the effective alternative hypothyroidism therapy to the levothyroxine treatment.

SUMMARY

The present invention provides an oriental medicine composition effective for thyroid disease treating through thyroid hormone level normalization.

According to an aspect of the present disclosure, the oriental medicine composition comprises Rehmanniae Radix Preparata, Angelicae Gigantis Radix, Lycii Fructus, Paeoniae Radix, and Dioscoreae Rhizoma. The oriental medicine composition according to the present disclosure may further comprise at least one selected from the group consisting of Bupeuri Radix, Poria Sclerotium, Atractylodis Rhizoma Alba, Lycii Radicis Cortex, Moutan Radicis Cortex, Anemarrhenae Rhizoma, Phellodendri Cortex, Fossilia Ossis Mastodi, Ostreae Testa, Glycyrrhizae Radix et Rhizoma, Cervi Parvum Cornu, and Hominis placenta.

The oriental medicine composition according to the present disclosure demonstrates the treatment efficacy of hypothyroidism or hyperthyroidism by normalizing the thyroid hormone level without side effects, unlike the conventional hormone control therapy, such as levothyroxine administration. In addition, the oriental medicine composition according to the present disclosure has the effect of sustaining the thyroid hormone concentration to be within the normal range for a long time just through constant-period administration.

DETAILED DESCRIPTION

Figure 1A:
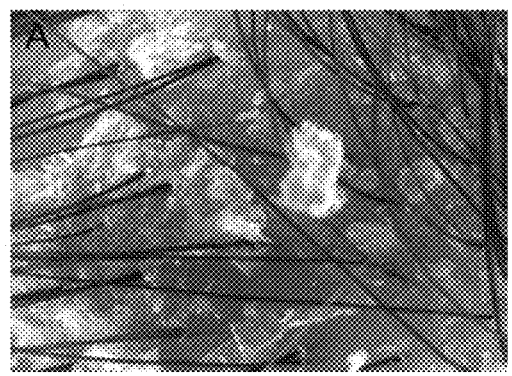
FIGS. 1A and 1B show photographs of the scalp of Patent 1 before and after administration of an oriental medicine composition according to the present disclosure, respectively.

Hereinafter, embodiments of the present disclosure will be described in detail. However, the present disclosure may not be limited to the following description, and various elements or features thereof may be changed or optionally combined in various manners, as necessary. Therefore, it is to be appreciated that all changes, equivalents or substitutes that do not depart from the spirit and technical scope of the inventive concept are encompassed in those embodiments of the present disclosure.

The oriental medicine composition according to the present disclosure comprises Rehmanniae Radix Preparata, Angelicae Gigantis Radix, Lycii Fructus, Paeoniae Radix and Dioscoreae Rhizoma. In addition, the oriental medicine composition according to the present disclosure may further comprise at least one from the group consisting of Bupeuri Radix, Poria Sclerotium, Atractylodis Rhizoma Alba, Lycii Radicis Cortex, Moutan Radicis Cortex, Anemarrhenae Rhizoma, Phellodendri Cortex, Fossilia Ossis Mastodi, Ostreae Testa, Glycyrrhizae Radix et Rhizoma, Cervi Parvum Cornu and Hominis placenta.

Various components of the oriental medicine composition will now be described.

Rehmanniae Radix Preparata is a herbal substance prepared by steaming followed by drying the dried Rehmanniae *glutinosa* after being dipped in alcohol, such as Huangjiu (yellow wine) or Baijiu (white wine). Various materials beneficial to the human body are newly generated in the course of steaming and drying the Rehmanniae *glutinosa*, and the more times the steaming and drying process is repeated, the higher quality of the Rehmanniae Radix Preparata can be obtained. Rehmanniae Radix Preparata improves deficiency of the body, replenishes the blood and is effective in treatment of menstrual irregularities, weak constitution, underdevelopment of children, dementia, premature ejaculation, or impotence.

Angelicae Gigantis Radix is a perennial herb belonging to the Umbellifer, has excellent effects of removing blood stasis by replenishing blood and assisting energy and blood circulation and relieving menstrual clamp and menstrual irregularities and ensuring postpartum recovery, which suggesting that Angelicae Gigantis Radix is beneficial to women. In addition, Angelicae Gigantis Radix contains vitamin B12 and folic acids, which is effective in prevention of anemia.

Lycii Fructus is a fruit from *Lycium chinense*, which belongs to the Solanaceae, and is abundant in betaine, one of the choline metabolites to prevent fatty liver syndromes by suppressing fat accumulation in the liver. In addition, Lycii Fructus contains vitamin C and rutin and has effects of strengthening blood vessels and preventing hypotension.

Paeoniae Radix is a perennial herb belonging to the Ranunculaceae, and is also called *Paeonia* Moutan. Paeoniae Radix has vitality refreshing and nourishing activities. In addition, Paeoniae Radix comprises paeoniflorin and paeonol, and thereby having analgesic, antipyretic, and anti-inflammatory activities and a blood pressure lowering effect.

Dioscoreae Rhizoma refers to tuber roots of Disocorea *japonica* or *Dioscorea batatas*, which belong to the *Dioscorea*. Dioscoreae Rhizoma has effects of increasing the appetite and treating indigestion, gastroenteric disorder, diabetes, coughing, lung disease, etc. In particular, Dioscoreae Rhizoma is excellent in strengthening kidney functions and the efficacy thereof is significantly superb when administering a person lacking in vigor.

Bupeuri Radix is a perennial herb, which belongs to the Apiaceae of the masterwort (*Peucedanum* ostruthium), and is also called north Bupeuri or Apioideae. The root of Bupeuri Radix contains saponin and fat oil, shows antipyretic, and anti-inflammatory activities, and has effects of treating flank pain, indigestion, nausea, and abdominal pain.

Poria Sclerotium refers to *sclerotium* of Wolfiporia extensa dried in the shade and is also called white solpungryung. Poria Sclerotium promotes diuretic activities, demonstrating the treatment efficacy of nephritis, cystitis or urethritis, and has an excellent sedative effect of calming stimulated nerves to then be used as a tranquilizer.

Atractylodis Rhizoma Alba is medicinal substance dried after removing the root-like stem of Atractylodes *japonica* Koidzumi or Atractylodes *macrocephala* Koidzumi. The Atractylodis Rhizoma Alba has peculiar smells, mildly sweet and bitter taste and warm nature. In cases of the systemic edema and indigestion caused by the stasis of body water, the Atractylodis Rhizoma Alba promotes water excretion and has anti-inflammatory, sedative and gastroprotective effects.

Lycii Radicis Cortex is the dried root-peel of *Lycium chinense*. The Lycii Radicis Cortex is effective in treating the cold sweat caused by a weak constitution, a cough, asthma, hematemesis, epistaxis, urinary hemorrhage, hyperglycemia, and hypertension, and has effects of relieving neuralgia, headache, shoulder pain, muscular pain, lumbago and so on. In addition, the Lycii Radicis Cortex exhibits cardiovascular blood pressure and glucose lowering activities.

Moutan Radicis Cortex refers to a herbal medicine made of the root-peel of Moutan peony of the Paeoniaceae. The Moutan Radicis Cortex has mildly bitter and hot taste and peculiar smells. The Moutan Radicis Cortex is helpful in relieving or treating symptoms of menstrual irregularities due to blood heat, menstrual cramps, hematemesis, epistaxis, spots, bone twinges caused by a consumptive fever, the elevation of blood pressure, bruise, abscesses, and appendicitis, and has effects of elimination of blood stasis, anti-inflammation and pain relief. In addition, The Moutan Radicis Cortex exhibits analgesic, sedative, antipyretic, anticonvulsant, anti-inflammatory, antithrombotic and antiallergic effects, inhibition of gastric secretions and uterine mucosal hemorrhages, and an antibacterial action.

Anemarrhenae Rhizoma is a Liliaceae plant and the root-like stem thereof can be used after drying under the sun. The Anemarrhenae Rhizoma is effective in lowering heat and relieving symptoms of thirst, stuffy feeling in the chest and restless limbs, and a decoction of the Anemarrhenae Rhizoma has excellent effects of treating symptoms of a cough, a dry cough, bone twinges, a fever, or a cold sweat. In addition, the Anemarrhenae Rhizoma exhibits antipyretic, nerve-calming, analgesic and sedative effects, adrenocorticotropic-hormone suppression, chronic bronchitis treatment, bile secretion, bacteriostasis and blood glucose level lowering activities.

Phellodendri Cortex is the dried peel of Phellodendron *amurense*, which belongs to the Rutaceae, and is also called yellow hard peel. The Phellodendri Cortex exhibits a blood glucose level lowering action and bacteriostatic activities on Diplococcus *Pneumoniae, Mycobacterium tuberculosis, Staphylococcus*, and is effective in preventing proliferation of tumor cells. In addition, the Phellodendri Cortex promotes secretion of gastric juice and improves appetite.

Fossilia Ossis Mastodi, which is a skeletal fossil of giant mammals, is mainly composed of calcium carbonate and has astringent taste and cold nature. The Fossilia Ossis Mastodi has anticonvulsant activity to be effect for treatment of seizure-related diseases and psychiatric diseases.

Ostreae Testa is dried oyster or oyster shells and has cold nature and salty taste. The Ostreae Testa contains a large amount of minerals, including calcium, sodium, magnesium, aluminum, potassium or phosphorus. In addition, Ostreae Testa contains propolis and flavonoid and thus exhibits anti-inflammatory, antibacterial and antioxidative activities.

Glycyrrhizae Radix et Rhizoma is a perennial herb, which belongs to the Fabaceae of the Rosales and has sweet taste. The Glycyrrhizae Radix et Rhizoma coordinates the toxicity of a medicine to make the efficacy of the medicine well manifested, controls cold heat of the intestinal organs and bad energy, promotes blood circulation, and strengthens muscles and bones. In addition, the Glycyrrhizae Radix et Rhizoma has detoxicating, muscle-relaxing, diuretic and anti-inflammatory functions, and exhibits effects of relieving and suppressing hepatitis, urticaria, dermatitis, eczema, or gastric ulcer.

Cervi Parvum Cornu refers to one obtained by cutting and drying the non-ossified or slightly ossified young horn of bucks, such as sika deer (*Cervus nippon*), red deer (*Cervus elaphus*), and Elk (*Cervus canadensis*), which belong to the Cervidae. The Cervi Parvum Cornu contains various effective ingredients, including free amino acids, polysaccharides, glycosaminoglycans (GAGs), hyaluronic acid, keratin, sialic acid, cholesterol, fatty acids, phospholipids, or inorganic elements. The Cervi Parvum Cornu is efficacious in growth promotion, hematopoiesis, protein synthesis promotion, blood cholesterol level lowering, immune activity enhancement and anti-aging functions.

Hominis placenta refers to the placenta taken from a healthy woman in childbirth, washed with clean water, warmed over the fire and then dried. The Hominis placenta strengthens resistance and thus is useful for the prevention of various chronic diseases including a tuberculosis, a neurasthenia and an anemia.

The amounts of the Rehmanniae Radix Preparata, Angelicae Gigantis Radix, Lycii Fructus, Paeoniae Radix, Dioscoreae Rhizoma, Bupeuri Radix, Poria Sclerotium, Atractylodis Rhizoma Alba, Lycii Radicis Cortex, Moutan Radicis Cortex, Anemarrhenae Rhizoma, Phellodendri Cortex, Fossilia Ossis Mastodi, Ostreae Testa, Glycyrrhizae Radix et Rhizoma, Cervi Parvum Cornu and Hominis placenta, are not particularly limited. For example, the oriental medicine composition according to the present disclosure may include, based on the total weight of the oriental medicine composition, 5 to 25 wt %, preferably 10 to 20 wt %, of Rehmanniae Radix Preparata, 2 to 20 wt %, preferably 5 to 15 wt %, of Angelicae Gigantis Radix, 2 to 20 wt %, preferably 5 to 15 wt %, of Lycii Fructus, 1 to 15 wt %, preferably 3 to 13 wt %, of Paeoniae Radix, 1 to 15 wt %, preferably 3 to 13 wt %, of Dioscoreae Rhizoma, 1 to 13 wt %, preferably 2 to 10 wt %, of Bupeuri Radix, 1 to 13 wt %, preferably 2 to 10 wt %, of Poria Sclerotium, 1 to 13 wt %, preferably 2 to 10 wt %, of Atractylodis Rhizoma Alba, 1 to 10 wt %, preferably 2 to 7 wt %, of Lycii Radicis Cortex, 1 to 10 wt %, preferably 2 to 7 wt %, of Moutan Radicis Cortex, 0.1 to 10 wt %, preferably 1 to 6 wt %, of Anemarrhenae Rhizoma, 0.1 to 10 wt %, preferably 1 to 6 wt %, of Phellodendri Cortex, 0.1 to 10 wt %, preferably 1 to 6 wt %, of Fossilia Ossis Mastodi, 0.1 to 10 wt %, preferably 1 to 6 wt %, of Ostreae Testa, 0.1 to 10 wt %, preferably 1 to 6 wt %, of Glycyrrhizae Radix et Rhizoma, 1 to 13 wt %, preferably 2 to 10 wt %, of Cervi Parvum Cornu, and 1 to 13 wt %, preferably 2 to 10 wt %, of Hominis placenta. When the amounts of the elements satisfy the ranges stated above, hypothyroidism or hyperthyroidism can be effectively treated by controlling thyroid stimulating hormone (TSH) and thyroxine (T4) levels to be normal ranges.

The oriental medicine composition can be used in the form of a hot-water extract obtained by extracting the composition in hot water in a general manner, or powder obtained by freeze-drying the hot-water extract. The formulation of the oriental medicine comprising the oriental medicine composition may not be particularly limited but may be one selected from the group consisting of, for example, liquids, pills, tablets, granules, capsules, health food, and health beverage.

Hereinafter, the present disclosure will be described in more detail with reference to Example. However, the following example is provided for illustrative purposes only, and the scope of the present disclosure should not be limited thereto in any sense.

EXAMPLE

Preparation of Oriental Medicine Extract 24 g of Rehmanniae Radix Preparata, 16 g of Angelicae Gigantis Radix, 16 g of Lycii Fructus, 12 g of Paeoniae Radix, 12 g of Dioscoreae Rhizoma, 8 g of Bupeuri Radix, 8 g of Poria Sclerotium, 8 g of Atractylodis Rhizoma Alba, 6 g of Lycii Radicis Cortex, 6 g of Moutan Radicis Cortex, 4 g of Anemarrhenae Rhizoma, 4 g of Phellodendri Cortex, 4 g of Fossilia Ossis Mastodi, 4 g of Ostreae Testa, 4 g of Glycyrrhizae Radix et Rhizoma, 8 g of Cervi Parvum Cornu, and 8 g of Hominis placenta 8 g, were mixed to prepared 152 g of the oriental medicine composition. The prepared oriental medicine composition was added to a decocting pot together with water in an amount about three times the weight of the oriental medicine composition, followed by decocting at about 100° C. for about three hours, yielding a desired oriental medicine extract.

Clinical Tests (1) Patient 1

The oriental medicine extract prepared in Example was administered to a 30-year old woman (Patient 1) who is suffering from seborrheic dermatitis and menstrual irregularities in daily administration three times a day for one month.

Before, 5 weeks and 13 weeks after administering the oriental medicine extract, thyroid stimulating hormone (TSH) and thyroxine (T4) levels were measured using a blood analyzer (I-Chroma™, Biotechmed Inc.), and the results thereof are shown in Table 1. As shown in Table 1, it could be confirmed that the TSH level was reduced and the thyroxine level was increased after the medicine extract comprising the oriental medicine composition according to the present disclosure was administered to a subject (Patient 1), and that the efficacy of the administered medicine extract was maintained 2 months even after completing the medicine administration.

Figure 1B:

In addition, the subject's scalp was observed by ultrasonography before and 13 weeks after administering the original medicine extract according to the present disclosure, and ultrasound images thereof are shown in FIG. 1. Before administering the original medicine extract according to the present disclosure, the subject's scalp was dark red and severely flaky, as shown in FIG. 1A. However, after administering the original medicine extract according to the present disclosure, the color of the subject's scalp became lighter and flakes were almost vanished, as shown in FIG. 1B. In addition, it was confirmed that scalp itchiness and back pain were improved from 10 to 3 and from 10 to 2, respectively, as scored in visual analogue scale (VAS), and that the subject's menstrual irregularities were improved.

(2) Patient 2

The oriental medicine extract prepared in Example was administered to a 55-year old woman (Patient 2) who suffered from hyperthyroidism and is suffering from fibromyalgia, shoulder and low back pain in daily administration three times a day for one month.

Before, 5 weeks and 13 weeks after administering the oriental medicine extract, thyroid stimulating hormone (TSH) and thyroxine (T4) levels were measured using a blood analyzer (I-Chroma™, Biotechmed Inc.), and the results thereof are shown in Table 1. As shown in Table 1, it could be confirmed that the TSH level was reduced and the thyroxine level was increased after the medicine extract comprising the oriental medicine composition according to the present disclosure was administered to a subject (Patient 2), and that the efficacy of the administered medicine extract was maintained 2 months even after completing the medicine administration. In addition, it was confirmed that fibromyalgia, shoulder and low back pain were reduced to 3, respectively, as scored in visual analogue scale (VAS), and that the subject's symptoms of fatigue, coldness and numbness were improved.

TABLE 1

|  |  | Patient 1 | Patient 2 |
| --- | --- | --- | --- |
| Pre-administration | TSH | 76.18 | 9.95 |
|  | T4 | 63.8 | 80.4 |
| 5 week after administration | TSH | 8.92 | 3.30 |
|  | T4 | 67.8 | 72.0 |
| 13 week after administration | TSH | 3.61 | 2.45 |
|  | T4 | 154.1 | 104.3 |

Preparation of Sample Powder

Sample 1: A mixture of 24 g of Rehmanniae Radix Preparata, 16 g of Angelicae Gigantis Radix, 16 g of Lycii Fructus, 12 g of Paeoniae Radix, 12 g of Dioscoreae Rhizoma, 8 g of Bupeuri Radix, 8 g of Poria Sclerotium, 8 g of Atractylodis Rhizoma Alba, 6 g of Lycii Radicis Cortex, 6 g of Moutan Radicis Cortex, 4 g of Anemarrhenae Rhizoma, 4 g of Phellodendri Cortex, 4 g of Fossilia Ossis Mastodi, 4 g of Ostreae Testa, and 4 g of Glycyrrhizae Radix et Rhizoma Sample 2: A mixture of Sample 1 and 8 g of Hominis placenta Sample 3: A mixture of Sample 1 and 8 g of Cervi Parvum Cornu Sample 4: 100% Chinese medicine formula called "xiao yao san"

Extracts obtained from the samples 1-4 were frozen at −80° C. and then dried. Each of the freeze-dried samples was filtered using a filter with a pore size of 0.45☐.

Experiments on Cells (1) Cell Culture

Rat thyroid cells (FRTL-5) were cultured in a Ham's F12 medium (American Type Culture Collection [ATCC], USA, to be referred to as "6H medium," hereinafter) comprising 6 species hormone mixture including 10 mU/ml of TSH, 0.01 mg/ml of insulin, 10 nM of hydrocortisone, 0.005 mg/ml of transferrin, 10 ng/ml of somatostatin, and 10 ng/ml of Gly-His-Lys acetate (Sigma, USA) with 0.5% newborn calf serum (Gibco) supplemented with 1% penicillin-streptomycin solution (Life Technologies, Waltham, Mass., USA) under 37° C. and 5% $CO_2$ conditions. The culture medium was replaced every 2 to 3 days, and the cells were sub-cultured at every 8-10 day interval.

(2) Cytotoxicity assay (TSH-excess condition)

Figure 2:
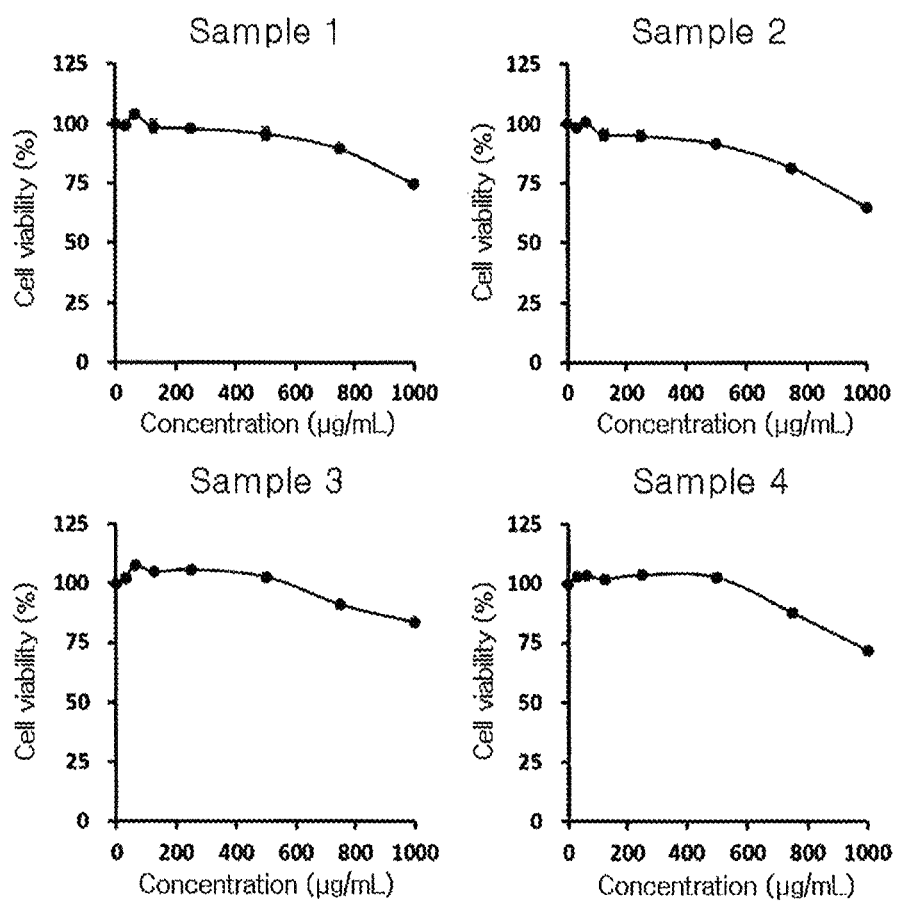
FIG. 2 is a graph showing cytotoxicity test results for the oriental medicine compositions according to the present disclosure under a TSH-excess condition.

FRTL-5 cells were separately transferred to 96-well plates, each including $2.5 \times 10^4$ cells, and then cultured in the 6H medium for 24 hours. Thereafter, each of the samples was diluted in the 6H medium with various concentrations of 15.125, 31.25, 62.5, 125, 250, 500, 750, and 1,000 μg/mL. After culturing for 24 hours, Ez-Cytox (DoGEN, Korea) was added for cytotoxicity assay, followed by culturing for 2 hours, and absorbance was measured at a wavelength of 450 nm. The absorbance was an average value taken from the experiments repeatedly conducted twice. The cytotoxicity of each sample was determined by obtaining the cell viability percentage calculated from a ratio of the absorbance of the treated sample group to the absorbance of the control group, and cell viability assay results are shown in FIG. 2. No significant changes in the cytotoxicity were observed until the samples were treated with the concentration of 500 μg/mL, and relatively high cytotoxicity of about 20% or greater was exhibited with concentrations of 750 μg/mL and 1,000 μg/mL.

(3) Determination of Thyroxine Levels (TSH-Excess Condition)

FRTL-5 cells were separately transferred to 96-well plates, each including $2.5 \times 10^4$ cells, and then cultured for 24 hours, and each of the samples was diluted in the 6H medium with concentrations of 250 μg/mL and 500 μg/mL, in which no cytotoxicity was exhibited from the samples. After culturing at 37° C. for 10 minutes, 1 nM-sodium iodine (NaI) was added to the medium, followed by further culturing for 3 hours, the supernatant of the cell culture medium was centrifuged using a centrifuge at a rate of 1,000 rpm for 5 minutes, and then recovered.

Figure 3:
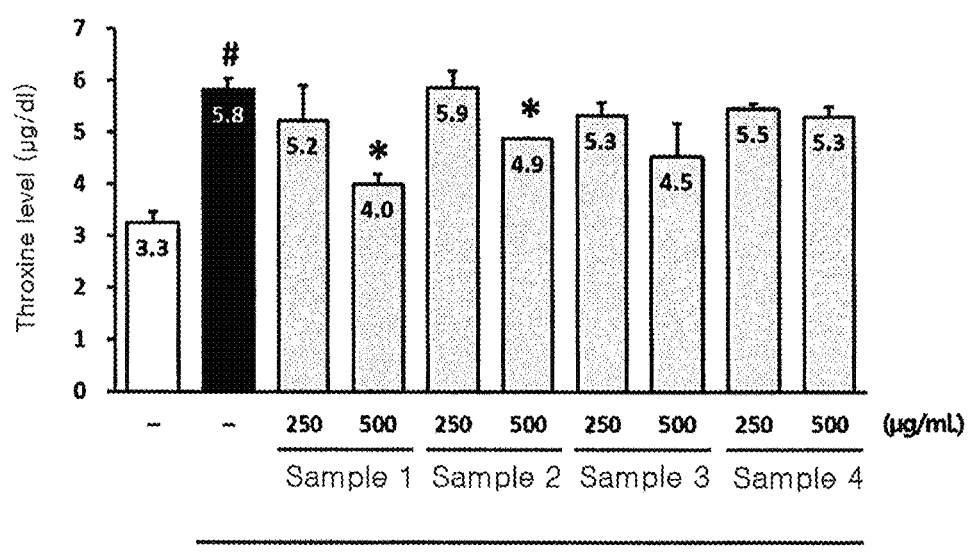
FIG. 3 is a graph showing the thyroxine secretion effects of the oriental medicine compositions according to the present disclosure under a TSH-excess condition.

50 μL of concentration-dependent standards and the supernatant sample were added to each well of micro well strips (T4 ELISA Kit, Biovision, USA), 100 μL of an enzyme conjugate was further added thereto, followed by agitating for 20 to 30 seconds, and the mixture was left undisturbed at room temperature for one hour. Then, the supernatant was entirely thrown away, and the respective wells were repeatedly washed with 300 μL of washing buffer three times. Then, 100 μL of a TMB substrate was added to the wells and then left undisturbed at room temperature for 15 minutes, followed by adding 50 μL of a stop solution and measuring the absorbance at 450 nm. The absorbance was an average value taken from the experiments repeatedly conducted twice, and the thyroxine levels are shown in FIG. 3. In addition, thyroxine levels of the treated sample group, calculated on the basis of the assumption that the thyroxine level of the iodine-treated group is 100%, are indicated in Table 2.

TABLE 2

| Sample | Concentration | Thyroxine level (%) |
| --- | --- | --- |
| Iodine-treated group | | 100.0 ± 3.4 |
| Sample 1 | 250 | 89.6 ± 11.5 |
| | 500 | 68.5 ± 3.5 |
| Sample 2 | 250 | 100.6 ± 5.5 |
| | 500 | 83.7 ± 0.3 |
| Sample 3 | 250 | 91.4 ± 4.2 |
| | 500 | 77.9 ± 10.9 |
| Sample 4 | 250 | 93.7 ± 1.5 |
| | 500 | 91.0 ± 3.3 |

As confirmed from Table 2 and FIG. 3, the samples 1-3 of the oriental medicine composition according to the present disclosure showed reduced thyroxine levels under the 6H medium condition (that is, under the TSH-excess condition). The thyroxine level reducing effect of the oriental medicine composition according to the present disclosure were higher than that of the xiao yao san (Sample 4) known to be effective in suppressing or relieving the thyroid disease.

(4) Cytotoxicity Assay (TSH-Deficient Condition)

Figure 4:
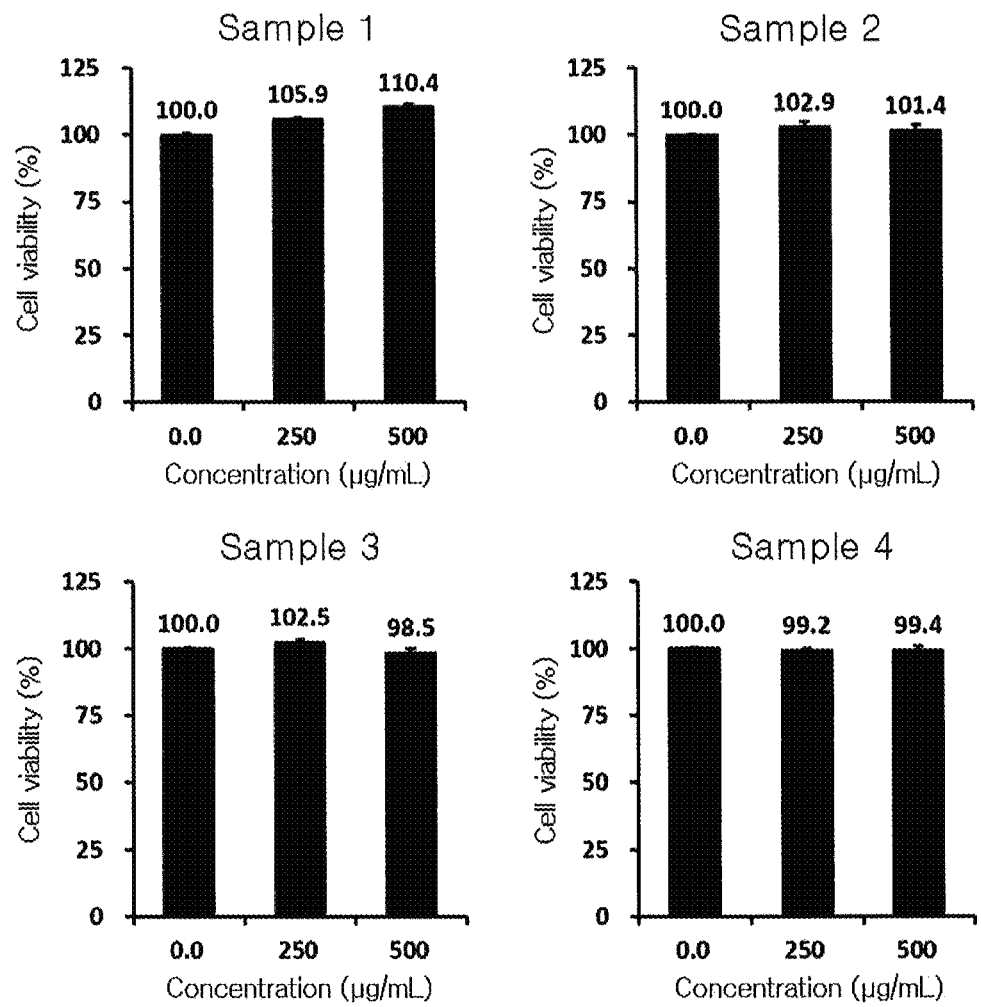
FIG. 4 is a graph showing the cytotoxicity test results for the oriental medicine compositions according to the present disclosure under a TSH-deficient condition.

FRTL-5 cells were separately transferred to 96-well plates, each including $2.5 \times 10^4$ cells, and then cultured in a medium without TSH (to be referred to as "5H medium," hereinafter) for 24 hours. Thereafter, each of the samples was diluted in the 5H medium with concentrations of 250 μg/mL and 500 μg/mL. After culturing for 24 hours, Ez-Cytox (DoGEN, Korea) was added for cytotoxicity assay, followed by culturing for 2 hours, and absorbance was measured at 450 nm. The absorbance was an average value taken from the experiments repeatedly conducted twice. The cytotoxicity of each sample was determined by obtaining the cell viability percentage calculated from a ratio of the absorbance of the treated sample group to the absorbance of the control group, and cell viability assay results are shown in FIG. 4. While the sample 1 demonstrated 5.9% and 10.4% in cell proliferation at concentrations of 250 μg/mL and 500 μg/mL, no significant changes in the cytotoxicity were observed.

(5) Determination of Thyroxine Levels (TSH-Deficient Condition)

FRTL-5 cells were separately transferred to 96-well plates, each including $2.5 \times 10^4$ cells, and then cultured for 24 hours. Thereafter, each of the samples was diluted in the 5H medium with concentrations of 250 μg/mL and 500 μg/mL. After culturing at 37° C. for 10 minutes, 1 nM-sodium iodine (NaI) was added to the medium, followed by further culturing for 3 hours, the supernatant of the cell culture medium was centrifuged using a centrifuge at a rate of 1,000 rpm for 5 minutes, and then recovered.

Figure 5:
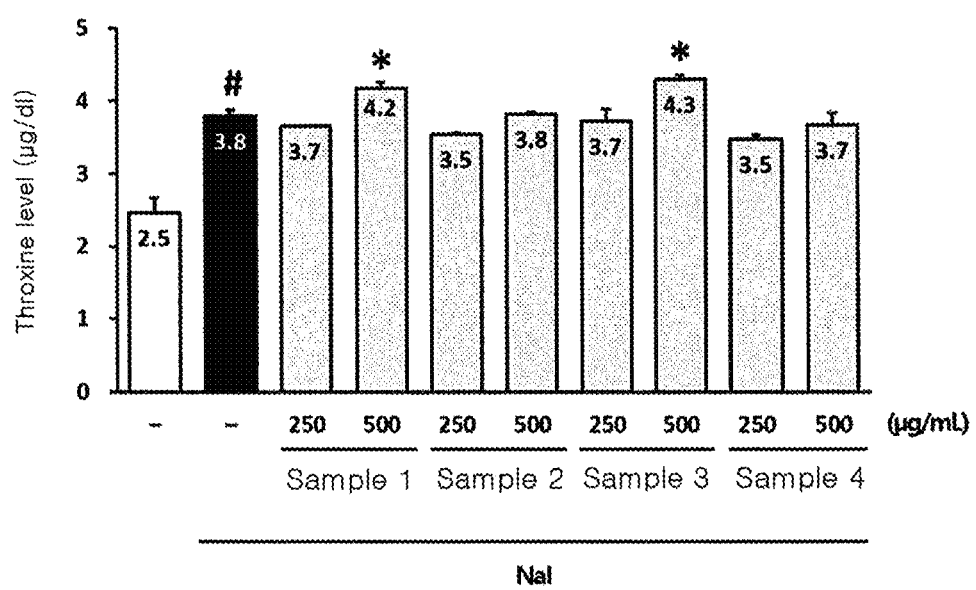
FIG. 5 is a graph showing the thyroxine secretion effects of the oriental medicine compositions according to the present disclosure under a TSH-deficient condition.

50 μL of concentration-dependent standards and the supernatant sample were added to each well of micro well strips (T4 ELISA Kit, Biovision, USA), 100 μL of an enzyme conjugate was further added thereto, followed by agitating for 20 to 30 seconds, and the mixture was left undisturbed at room temperature for one hour. Then, the supernatant was entirely thrown away, and the respective wells were repeatedly washed with 300 μL of washing buffer three times. Then, 100 μL of a TMB substrate was added to the wells and then left undisturbed at room temperature for 15 minutes, followed by adding 50 μL of a stop solution and measuring the absorbance at 450 nm. The absorbance was an average value taken from the experiments repeatedly conducted twice, and the thyroxine levels are shown in FIG. 5. In addition, thyroxine levels of the treated sample group, calculated on the basis of the assumption that the thyroxine level of the iodine-treated group is 100%, are indicated in Table 3.

TABLE 3

| Sample | Concentration | Thyroxine level (%) |
|---|---|---|
| Iodine-treated group | | 100.0 ± 2.3 |
| Sample 1 | 250 | 96.5 ± 0.0 |
| | 500 | 110.1 ± 2.0 |
| Sample 2 | 250 | 93.8 ± 0.3 |
| | 500 | 100.8 ± 0.8 |
| Sample 3 | 250 | 98.0 ± 4.5 |
| | 500 | 113.2 ± 1.7 |
| Sample 4 | 250 | 91.7 ± 1.3 |
| | 500 | 96.7 ± 4.5 |

As confirmed from Table 3 and FIG. 5, the samples 1-3 of the oriental medicine composition according to the present disclosure showed increased thyroxine levels under the 5H medium condition (that is, under the TSH-deficient condition). The thyroxine level increasing effect of the oriental medicine composition according to the present disclosure were higher than that of the xiao yao san (Sample 4) known to be effective in suppressing or relieving the thyroid disease.

What is claimed is:

1. An oriental medicine composition for treating thyroid diseases comprising: 5 to 25% by weight of Rehmanniae Radix Preparata, 2 to 20% by weight of Angelicae Gigantis Radix, 2 to 20% by weight of Lycii Fructus, 1 to 15% by weight of Paeoniae Radix, 1 to 15% by weight of Dioscoreae Rhizoma, 1 to 13% by weight of Bupeuri Radix, 1 to 13% by weight of Poria Sclerotium, 1 to 13% by weight of Atractylodis Rhizoma Alba, 1 to 10% by weight of Lycii Radicis Cortex, 1 to 10% by weight of Moutan Radicis Cortex, 0.1 to 10% by weight of Anemarrhenae Rhizoma, 0.1 to 10% by weight of Phellodendri Cortex, 0.1 to 10% by weight of Fossilia Ossis Mastodi, 0.1 to 10% by weight of Ostreae Testa, 0.1 to 10% by weight of Glycyrrhizae Radix et Rhizoma, 1 to 13% by weight of Cervi Parvum Cornu, and 1 to 13% by weight of Hominis placenta, based on the total weight of the oriental medicine composition.

2. An oriental medicine for treating thyroid diseases comprising the oriental medicine composition according to claim 1.

3. The oriental medicine of claim 2, wherein the oriental medicine is hot-water extract of the oriental medicine composition or freeze-dried powder of the hot-water extract.

4. The oriental medicine of claim 2, wherein the oriental medicine is produced in the form of one formulation selected from liquids, pills, tablets, granules, capsules, health food, and health beverage.

* * * * *